United States Patent [19]
Holub et al.

[11] Patent Number: 5,811,616
[45] Date of Patent: Sep. 22, 1998

[54] $BF_3$ GAS RECOVERY PROCESS

[75] Inventors: Richard A. Holub; Scott D. Soltis, both of Houston, Tex.

[73] Assignee: Amoco Corporation, Chicago, Ill.

[21] Appl. No.: 489,880

[22] Filed: Jun. 13, 1995

[51] Int. Cl.$^6$ .................... C07C 2/08; C07C 2/26
[52] U.S. Cl. ............... 585/504; 585/520; 585/521; 585/525; 423/293
[58] Field of Search ................. 585/504, 520, 585/521, 525; 423/293

[56] References Cited

U.S. PATENT DOCUMENTS

| | | | |
|---|---|---|---|
| 4,032,591 | 6/1977 | Cupples et al. . | |
| 4,227,027 | 10/1980 | Booth et al. | 585/525 |
| 4,239,930 | 12/1980 | Allphin et al. | 585/525 |
| 4,263,467 | 4/1981 | Madgavkar et al. | 585/525 |
| 4,409,415 | 10/1983 | Morganson et al. | 585/525 |
| 4,520,225 | 5/1985 | Marty et al. | 585/525 |
| 4,956,512 | 9/1990 | Nissfolk et al. | 585/521 |
| 4,956,513 | 9/1990 | Walker et al. | 585/525 |
| 4,981,578 | 1/1991 | Tycer et al. | 208/262.1 |
| 4,982,042 | 1/1991 | Akatsu et al. | 585/525 |
| 5,180,403 | 1/1993 | Kogure | 55/53 |
| 5,254,784 | 10/1993 | Nurminen et al. | 585/525 |

*Primary Examiner*—Elizabeth D. Wood
*Attorney, Agent, or Firm*—James R. Henes; Stephen L. Hensley

[57] ABSTRACT

$BF_3$ is vaporized from specified crude polyolefin reaction product mixture in a vaporization zone at a temperature insufficient to decompose $BF_3$ or any $BF_3$ promoter complex in the mixture, and the vaporized $BF_3$ may be recovered directly. Further, a process for the oligomerization of a liquid olefin composition and recovery of $BF_3$ is described in which inert volatile material present in a liquid olefin composition is removed from the composition by vaporization, forming a degassed liquid olefin composition free of inert volatile material. The degassed liquid olefin composition is then contacted in a reaction zone with $BF_3$ under conditions to oligomerize the olefin, forming crude polyolefin oligomerization reaction product mixture containing dissolved $BF_3$, which may be treated as described.

10 Claims, 2 Drawing Sheets

BF$_3$ GAS RECOVERY PROCESS

FIELD OF THE INVENTION

The invention relates to the improved utilization or recovery of boron trifluoride (BF$_3$) in a process for the oligomerization of an olefin or olefin-containing mixture wherein BF$_3$ is employed as a catalyst or catalyst component. In particular, the invention concerns the recovery of boron trifluoride (BF$_3$) from crude reaction product mixture derived from the oligomerization of an olefin or olefin-containing mixture.

BACKGROUND OF THE INVENTION

The production of oligomers from olefin or olefin-containing mixtures, particularly from alpha olefins, is well known, as is the use of the oligomerization product or products in a variety of lubricants and functional fluids. In preferred processes for the oligomerization of olefins, boron trifluoride is employed as a catalyst for the oligomerization reaction. However, because BF$_3$ is a relatively slow catalyst, a "promoter" or co-catalyst composition, which may be selected from a wide variety of materials, is commonly employed with the BF$_3$ to improve reaction rates.

In at least one process utilizing BF$_3$ and a promoter, the promoter composition, e.g., an oxygenated organic material, such as an alkanol, is believed to form a stable complex or adduct with BF$_3$ supplied to the reaction zone. Preferably, the BF$_3$ is supplied to the reaction zone in an excess of that required for formation of the complex. In the case of such oxygen-containing promoter, for example, the BF$_3$ is commonly supplied in a ratio of from about 1.0 moles to about 4.0 moles of BF$_3$ per mole of oxygen atoms in the compound, although there is no actual limit. The excess BF$_3$ is believed to be loosely associated with the complex, or may simply be dissolved in the reaction mixture, and is susceptible to the recovery procedure of the invention.

Prior to the invention, in at least one olefin oligomerization process utilizing BF$_3$ and promoter, the BF$_3$ catalyst remaining in the oligomerization reaction product mixture, upon recovery of the mixture, has represented a significant cost/disposal problem. That is, BF$_3$ recovery in a reusable form from the reaction product mixture has been difficult because of the unusual properties of BF$_3$ and the nature of oligomerization chemistry. As a result, rather than attempt recovery of the BF$_3$, the catalyst has been treated in a variety of ways, such as by reaction thereof with an ammonium or alkali metal compound, followed by appropriate disposal of the reaction product. However, increasing environmental consciousness has spurred efforts to develop methods to reclaim such byproducts and thereby minimize environmental impact. Additionally, the loss of such a valuable catalytic material by disposal directly impacts the economics of the oligomerization process. Accordingly, a need has existed for recovering BF$_3$ values from oligomer reaction systems or mixtures. The invention addresses this need.

SUMMARY OF THE INVENTION

In one embodiment, therefore, the invention relates to a process in which a specified crude polyolefin-containing oligomerization reaction product liquid or liquid mixture, described more fully hereinafter, containing dissolved BF$_3$, is recovered and the dissolved BF$_3$ is vaporized therefrom in a vaporization zone. By the practice of the invention, vaporized BF$_3$ may be returned directly to the reaction zone producing the crude polyolefin-containing reaction mixture, or some or all of the vaporized BF$_3$ may be sent to one or more reaction zones in a multi-reaction zone process. As used herein, the term "crude oligomerization reaction product mixture" is understood to refer to a liquid polyolefin-containing product mixture derived or obtained from a reaction zone or zones wherein a liquid olefin is oligomerized in the presence of BF$_3$, as described more fully hereinafter. Additionally, the term "dissolved BF$_3$" is understood to refer not only to BF$_3$ that is dissolved in the reaction mixture but to include that BF$_3$ which may be loosely chemically held in the mixture. In this regard, evidence exists that BF$_3$ exists in the reaction mixture in different degrees of association. While not wishing to be bound by any theory of invention, it appears that BF$_3$ forms, on an equimolar basis, a strongly bonded complex with components of various promoter materials, e.g., the oxygen in oxygen-containing compounds. This complex is not readily removed by vaporization from the reaction mixture. Additional BF$_3$ in or added to the reaction mixture appears to be dissolved therein or only lightly bonded to the promoter or component thereof, and is susceptible to the recovery procedure of the invention. The invention is thus applicable to oligomerization processes that employ a promoter, as well as those where a promoter or co-catalyst is not employed.

In order to send the BF$_3$ vaporized from the crude oligomerization reaction product mixture to a desired reaction zone or reactor, however, difficulties related to the pressure relationships in the respective units must be overcome. That is, if BF$_3$ is vaporized from a crude polyolefin-containing oligomerization reaction product liquid or liquid mixture in a zone or vessel having a pressure reduced or maintained at a level to induce the vaporization or flashing of the BF$_3$ from the crude reaction product mixture, returning the BF$_3$ to an oligomerization reactor, which is normally operated under significantly higher pressure, requires a stepup in pressure. Unfortunately, inert volatile or gaseous material, which is commonly present or dissolved in the crude oligomerization reaction product mixture from which the BF$_3$ is to be vaporized, will also be released and will require compression, and a pressure buildup or head will result in a reactor if this material is not separated from the BF$_3$ before entry into the reactor or if the inert volatile material is not somehow purged from the system. The inert volatile material or component, which is understood herein to comprise principally inert gas such as nitrogen, and perhaps minor quantities of other volatile substances or compounds which are non-interfering in the olefin reaction, is present by dissolution in the liquid olefin composition, or is in a loose form of association therein.

In studying the problem of inert volatile material in the crude oligomerization product mixture, analysis determined that, in at least one process for the oligomerization of an olefin composition, the liquid olefin composition feed is an important source of the inert volatile material. In particular, in the case of one process for oligomerization of 1-decene, the 1-decene or 1-decene-containing feed is stored under nitrogen. Further research indicates that nitrogen has a significant solubility in the 1-decene, e.g., 0.28 wt. percent at 10° C. Accordingly, if the crude oligomerization reaction product mixture from the oligomerization reactor of this process is flashed, in the absence of the invention, nitrogen dissolved therein during storage will be released and will create the difficulties mentioned.

The invention, therefore, proceeds from the realization that pressure buildup may be reduced and direct recovery or transfer of the dissolved BF$_3$ may be accomplished if the source for the inert volatile material in the crude oligomerization reaction product mixture is eliminated. In one aspect, therefore, the invention accomplishes this by utilization of olefin feed materials that are free of inert volatile materials by, for example, proper choice of olefin sources, or, by use of storage gases having limited solubility in the olefin, e.g., helium, argon, etc., so that the crude oligomerization reaction product mixture is free of inert volatile materials. Preferably, however, the problem is overcome in the normal case by the provision of a novel degassing procedure prior to introduction of the liquid olefin composition into the reactor or reaction zone. This innovation may be accompanied by appropriate periodic or continuous purge of the $BF_3$ recovery system to insure proper pressure control.

Accordingly, in a principal embodiment of the invention, the invention relates to a process for the oligomerizeration of a liquid olefin composition in which, prior to the introduction of the olefin composition into a reaction zone, the liquid olefin composition is degassed to remove inert volatile material present therein. A liquid olefin composition which is free (i.e., little or no content) of such inert volatile material is produced which is then oligomerized in the presence of $BF_3$, and preferably $BF_3$-promoter complex or co-catalyst, under suitable conditions, to produce a crude oligomerization reaction product mixture containing oligomerized olefin and dissolved $BF_3$ (and $BF_3$-promoter complex, if employed). Crude reaction product mixture, free of inert volatile material, is removed from the reaction zone and is forwarded to a vaporization zone where the dissolved $BF_3$ is vaporized. Part or all the vaporized $BF_3$ is then returned to the reaction zone producing the crude reaction mixture, or, alternately, to one or more reactors or zones utilizing $BF_3$ catalyst.

In more specific aspects of the invention, suitable means, such as a liquid sealed rotary pump or pumps, or an ejector pump, or pumps, or similar means, in which a liquid ring seal in the rotary pump(s) or a fluid moment in the ejector pump(s) is obtained by an olefin containing $BF_3$, are provided for the recycle or forwarding of the $BF_3$ to the reaction zones. Finally, proper pressure balance in the system is maintained, suitably by provision of means for purging or releasing pressure buildup. In a preferred embodiment, the invention relates to a process for the oligomerization of a liquid olefin in the presence of a $BF_3$ catalyst and promoter, the invention being characterized by degassing of the liquid olefin composition feed, removal of crude reaction product mixture, and treatment as described to recover dissolved $BF_3$.

BRIEF DESCRIPTION OF THE DRAWING

The drawings are schematic illustration of the process flow type.

DETAILED DESCRIPTION OF THE INVENTION

Figure 1:
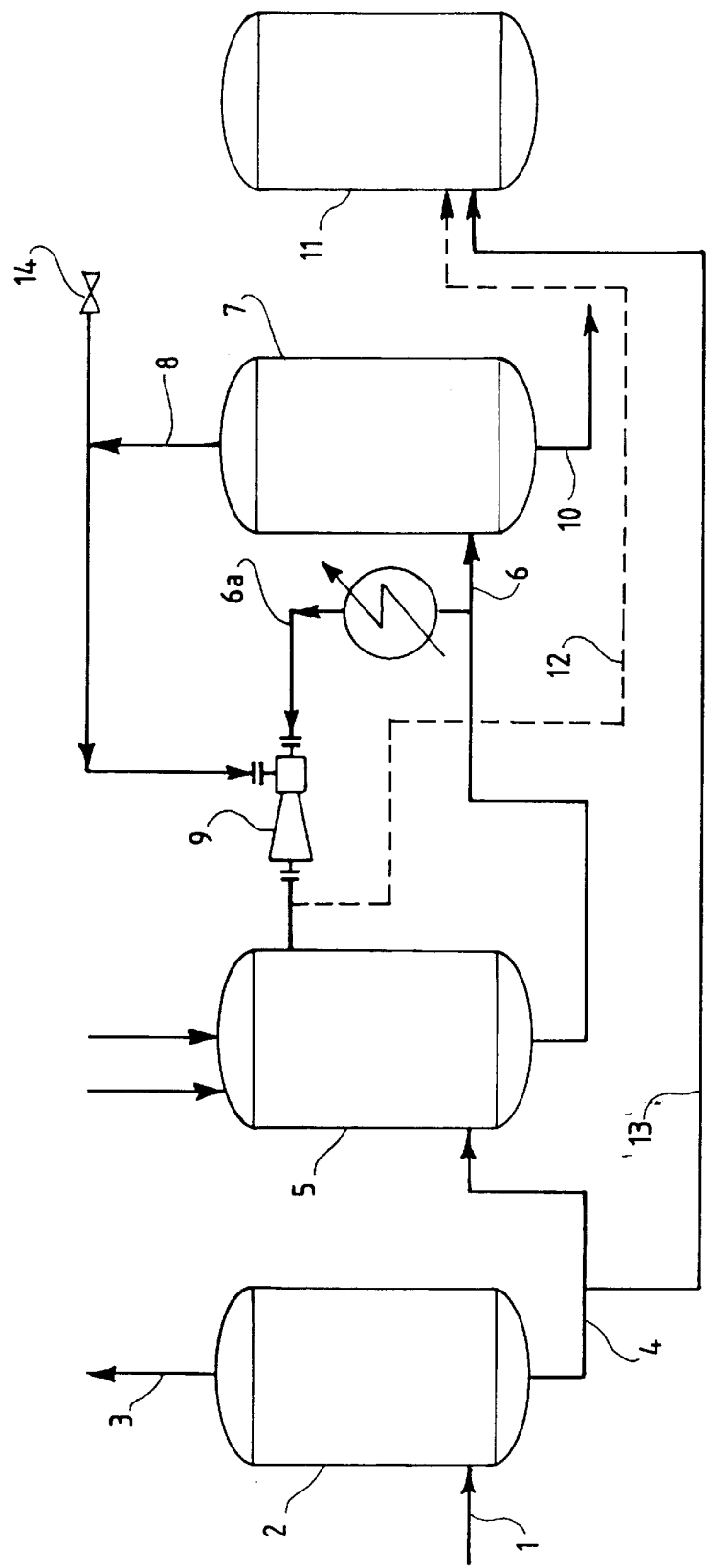
FIG. 1 illustrates the initial degassing step with an ejector pump being utilized for the return of the $BF_3$.

Processes for the oligomerization of an olefin or olefins utilizing $BF_3$ and a promoter are well known, as exemplified in U.S. Pat. No. 4,981,578, U.S. Pat. No. 4,032,591, and U.S. Pat. No. 4,409,415. Accordingly, only sufficient description of the reaction procedure is provided as is necessary for an understanding of the invention. Olefins commonly oligomerized by such procedures include linear and branched $C_4$ to $C_{30}$ olefins, preferably $C_6$ to $C_{20}$, which may be alpha or internal olefins, and mixtures thereof. Alpha olefins, and mixtures thereof, are preferred, particularly those containing 8 through 12 carbon atoms. The most preferred is 1-decene, usually supplied as a 1-decene composition which may be the pure or substantially pure material or a mixture comprising a substantial portion, say at least fifty percent by weight of 1-decene, such as a 75 weight percent mixture of 1-decene and other olefins. For simplicity, as used hereinafter, the term "olefin composition" is understood to include an olefin, a mixture of olefins, or an olefin- or olefins- containing composition, of the types above-mentioned, encompassing the presence, even in major amounts, of non-interfering or at least substantially non-interfering species, e.g., alkanes, in the composition. The term "1-decene composition", in a similar vein, is taken to include compositions ranging from "pure" 1-decene to mixtures with other olefins, or mixtures thereof, and includes, as noted, the presence, even in major amounts, of non-interfering or at least substantially non-interfering species, in the composition. Again, unless otherwise indicated or inconsistent with the circumstances, all percentages of components of a mixture expressed herein are by weight, based on the total weight of the mixture.

As mentioned, an important embodiment of the invention includes the degassing of the liquid olefin composition before entry thereof into the reactor or reactors. According to the invention, dissolved nitrogen and other inert volatile substances, present in the liquid olefin composition, are vaporized prior to introduction of the liquid olefin composition into the reaction zone. The vaporization may be accomplished by any suitable combination of temperature and pressure. Preferably, vaporization is accomplished by heating the liquid olefin composition to a suitable temperature, e.g., from about 10° C. to about 170° C., preferably from about 10° C. to 80° C., at atmospheric or reduced pressure, and allowing the nitrogen and other inert volatile material to flash therefrom.

In general, the oligomerization reaction is carried out by combining the liquid olefin composition and $BF_3$, preferably with the $BF_3$-promoter complex, in a reaction zone under suitable reaction conditions. Variation of reaction conditions is known to affect the character of the reaction product obtained; an oligomer of desired composition and properties may be obtained, for example, by regulating the temperature of the reaction. In this regard, the reaction will be conducted at suitable temperatures, e.g., from about −20° C. to about 90° C., with temperatures within the range of from about 20° C. to about 90° C. being preferred. Similarly, pressures in the reactor may be varied, but normally will range from one atmosphere to about ten atmospheres, with pressures of from about 1.5 atmospheres to about 5 atmospheres being preferred.

Any of the known promoters that form a complex with $BF_3$ may be used. For example, straight and branched alkanols of 1 through 20 carbon atoms, (such as methanol, ethanol, n-propanol, isobutanol, n-hexanol, 2-ethylhexanol, n-decanol, n-dodecanol, and the like), and mixtures thereof, may be used. Also, water, fatty acids, i.e., hydrocarbyl acids containing from 1 to 20 carbon atoms (such as valeric, caproic, and the like), and mixtures thereof, organic esters (such as butyl acetate, methyl valerate, ethyl octanoate, and the like) and mixtures thereof, ketones (e.g., methyl ethyl ketone, methyl isobutyl ketone, and the like) and mixtures thereof, ethers (e.g., dibutyl ether, tetrahydrofuran, dioxane, and the like) and mixtures thereof, alkoxylated alkanols (such as 2-methoxyethanol, 2-ethoxyethanol, and the like) and mixtures thereof, polyhydric alcohols (e.g., glycol, glycerol, and the like) and mixtures thereof, inorganic acids (e.g., phosphoric and the like) and mixtures of such acids, silica, zeolites, and the like. Preferred promoters are straight and branched chain alkanols containing from 1 through 8 carbons, with straight and branched chain alkanols containing from 2 through 5 carbons being most preferred. The promoter-complex and/or $BF_3$ is present in a catalytic amount, as understood by those skilled in the art.

As mentioned, dissolved $BF_3$ in the crude reaction product mixture removed from the oligomerization reaction zone is vaporized from the crude reaction product mixture. The vaporization may be accomplished by any suitable combination of temperature and pressure. The temperature utilized will be a temperature sufficient to vaporize dissolved $BF_3$ from the crude oligomerization reaction product mixture, but insufficient to decompose or dissociate $BF_3$. If a promoter or co-catalyst complex is present in the mixture, the vaporization temperature will be insufficient to dissociate or decompose the $BF_3$-promoter or co-catalyst complex. As used herein, the expressions "insufficient to decompose" and "insufficient to dissociate", in the context of the vaporization procedure of the invention, are understood to permit or allow minor or very minor decomposition or dissociation of the $BF_3$-promoter complex or co-catalyst, provided at least the bulk of the complex or co-catalyst remains undissociated or combined. Preferably, vaporization is accomplished by heating the liquid oligomerization reaction product mixture to a suitable temperature and allowing the $BF_3$ to flash therefrom at atmospheric or reduced pressure. In general, temperatures of from about 10° C. to about 80° C. will release the $BF_3$ at atmospheric or below atmospheric pressure, with temperatures within the range of from about 20° C. to about 80° C. being preferred at the pressures mentioned. The relatively low temperatures for vaporization have the great advantage of minimizing undesirable effects on the oligomer in the crude reaction product mixture. Additionally, as a practical matter, since the $BF_3$ is to be reabsorbed or captured, lower temperatures in the range are desirable. The vaporization may be carried out in a zone or vessel which is "dedicated" to a specific oligomerization reactor or reaction zone, or, if multiple reactors or reaction zones are employed, a common vaporization vessel or zone may be used to vaporize the $BF_3$ from reaction mixture from multiple reaction zones.

Upon vaporization, the $BF_3$ passes or is preferably forwarded by suitable means to the desired reaction zone. Thus, for example, a liquid jet pump or pumps may be used to pull vacuum on the $BF_3$ vaporized (the pump or pumps may actually aid vaporization), and will discharge part or all of the $BF_3$ into the reactor from which it came and/or to one or more other reactors. Similarly, if a liquid ring vacuum pump or pumps are utilized, preferably with liquid olefin as the sealing fluid, the $BF_3$ vapor may be sent to any desired reactor or reactors. In this regard, those skilled in the art will recognize that multiple reaction zones, with separate, independent, or combined feeds are common, so that the location to which part or all of the vaporized $BF_3$ is sent will depend on a variety of considerations, and the $BF_3$ could even be recovered for other uses.

In order to describe the invention more fully, the following illustration is made utilizing the accompanying drawing. In this illustration, all values given are calculated or merely exemplary, and the procedure is assumed to be continuous.

Accordingly, in FIG. 1, a liquid olefin-containing stream, e.g., a stream of 1-decene (75 percent 1-decene monomer, 25 percent other olefins and inert material) in line 1 enters degassing zone or vessel 2 where the inert volatile component therein (principally nitrogen) is removed or vaporized by heat or a combination of heat and pressure. In particular, the nitrogen may be removed by heating the stream, e.g., to 100° C. at atmospheric pressure, or if it is not desired to heat the stream, by use of vacuum at ambient temperature. The inert volatile material is removed overhead via line 3, and the 1-decene monomer stream is sent via line 4 to reactor 5 where it is contacted with $BF_3$ and a promoter such as propanol. Reactor 5, although illustrated as a single vessel, is preferably a series of vessels with independent feeds of $BF_3$ to each vessel, reacting liquid passing from one vessel to the next in the series, with crude oligomerization reaction product mixture being removed from the last vessel. The contacting is carried out under suitable conditions, e.g., 100° F. and 44 psig pressure, to oligomerize the olefin, accompanied by intimate mixing of the olefin and catalysts, total contact time being, for example, 2 to 3 hours. As illustrated, a crude oligomerization reaction product mixture containing polydecene, dissolved $BF_3$, and $BF_3$-promoter is removed from the bottom of reactor 5 and forwarded via line 6 to a flash or vaporization zone 7. Line 6a provides crude reaction product liquid to jet pump 9, as described more fully hereinafter. Flash zone 7 comprises a simple tank where the $BF_3$ is flashed from the crude reaction mixture by suitable temperature-pressure conditions. For example, prior to entry into zone or vessel 7, the crude oligomerization reaction mixture may be heated (not illustrated in the drawing) to a temperature of 700° C., so that upon entry into tank 7, which is operated a slightly below atmospheric pressure by action of suction from line 8 pulled by jet pump 9, the $BF_3$ in the mixture flashes from the crude reaction product mixture and passes overhead into line 8. The remaining crude reaction product mixture, containing polydecene and $BF_3$-complex, is removed from flash zone 7 via line 10 to further treatment and/or recovery of the contents thereof. A portion or all of the $BF_3$ in line 8 may be returned to one or more reactors of reaction zone 5 by jet pump 9, or alternately, may be sent partially or completely to a further reactor 11 (dotted line 12). Reactor 11 may be fed by line 13 which contains degassed 1-decene from degassing unit 2. A purge valve or similar means 14 is provided for regulation of pressure in line 8. Effective degassing of the liquid olefin feed and, perhaps, minor purge control, permits direct return or forwarding of $BF_3$ to the reaction zone or zones and efficient and economic recovery of dissolved $BF_3$ from the crude reaction product mixture. Although not illustrated, the crude reaction product mixture from 11 may be treated in a similar fashion to that from reactor 5, to the end that economic utilization of $BF_3$ is obtained.

Figure 2:
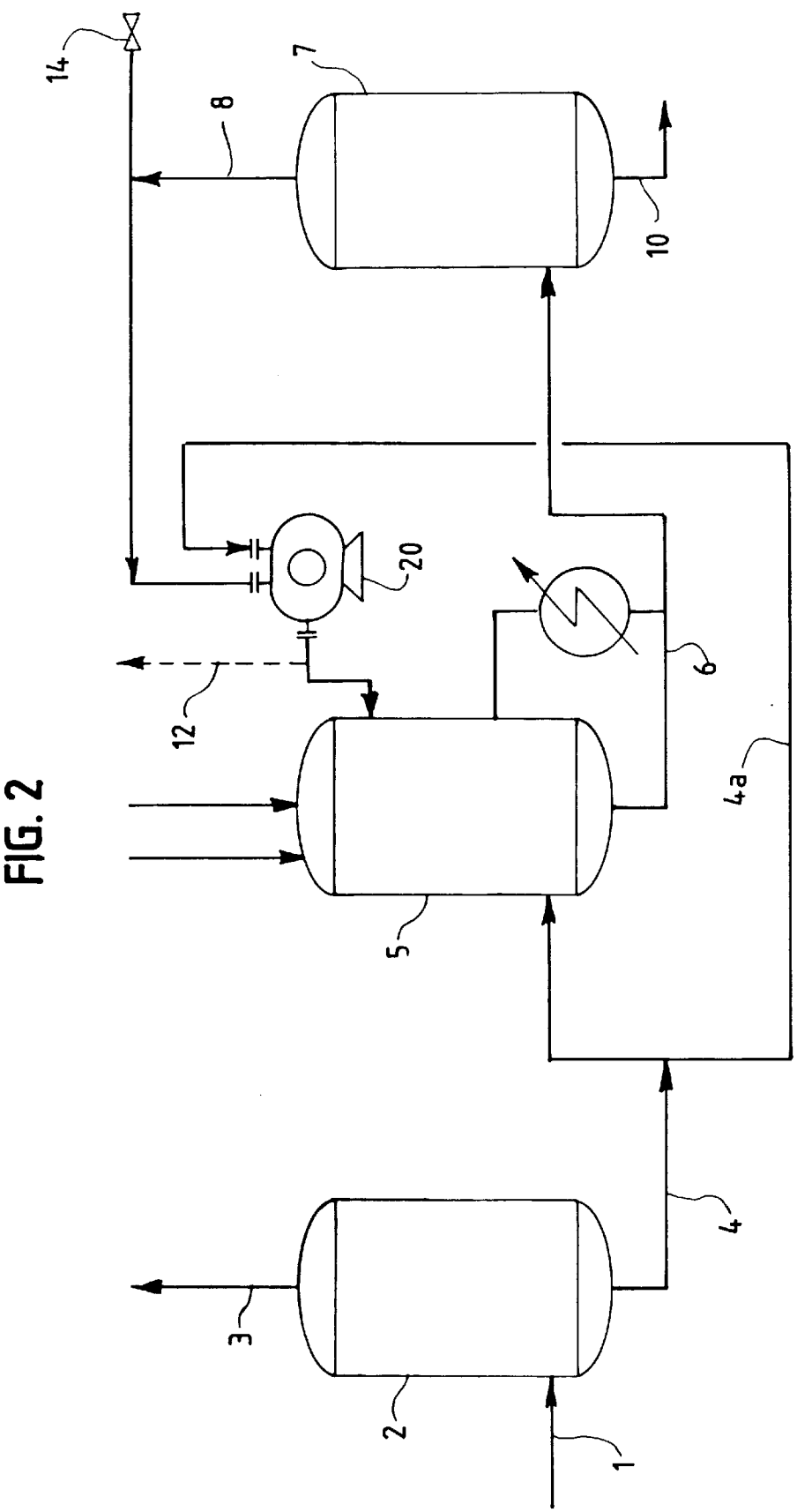
FIG. 2 further illustrates the use of a liquid ring seal pump and the use of a slip stream of degassed liquid olefin-$BF_3$ mixture for forming the seal of the pump.

In FIG. 2, feed and degassing of a 1-decene stream proceeds in elements 1, 2, and 3 as previously described. However, a slip stream 4a of the degassed 1-decene is taken from line 4 and forwarded to liquid ring vacuum pump 20, to the end that a seal of liquid 1-decene is provided in pump 20. All other elements shown operate in a manner similar to that of FIG. 1. Pump 20 serves to return or forward $BF_3$, as desired.

While the invention has been illustrated with particular apparatus, those skilled in the art will appreciate that, except where specified or otherwise required, other equivalent or analogous units may be employed. For example, vacuum pumps or combinations of vacuum pumps, eductors, and liquid seal pumps may be used. As indicated, the terms "zone" or "zones", as employed in the specification and claims, include, where suitable, the use of segmented equipment operated in series, or the division of one unit into multiple units because of size constraints, etc.

What is claimed is:

1. A process for the oligomerization of a liquid olefin composition and the recovery of $BF_3$, comprising: removing inert volatile material present in a liquid olefin composition from the composition by vaporization, forming a degassed liquid olefin composition feed that is free of inert volatile material;

contacting the resulting degassed liquid olefin composition feed in a reaction zone with $BF_3$ under conditions to oligomerize olefin in said degassed liquid olefin composition feed, thereby forming crude polyolefin oligomerization reaction product mixture containing dissolved $BF_3$;

vaporizing $BF_3$ from said crude polyolefin reaction product mixture in a vaporization zone at a temperature insufficient to decompose $BF_3$ or any $BF_3$ promoter complex in said mixture; and recovering $BF_3$ vaporized in said vaporization zone, free of the aforesaid inert volatile material.

2. The process of claim 1 wherein recovered $BF_3$ is returned to the reaction zone.

3. The process of claim 1 wherein the liquid olefin composition is a liquid $C_6$ to $C_{20}$ olefin composition.

4. The process of claim 1 wherein recovered $BF_3$ is sent to a reaction zone.

5. A process for the oligomerization of an 1-decene composition and the recovery of $BF_3$, comprising: removing inert volatile material present in liquid 1-decene composition from the composition by vaporization, forming a degassed liquid 1-decene composition feed that is free of inert volatile material;

contacting the resulting degassed liquid 1-decene composition feed with $BF_3$ in a reaction zone under conditions to oligomerize 1-decene, thereby forming crude polydecene oligomerization reaction product mixture containing dissolved $BF_3$;

vaporizing $BF_3$ from the crude polydecene oligomerization reaction product mixture in a vaporization zone at a temperature insufficient to decompose $BF_3$ or any $BF_3$ promoter complex in said mixture; and recovering $BF_3$ vaporized in said vaporization zone, free of the aforesaid inert volatile material.

6. The process of claim 5 wherein recovered $BF_3$ is returned to the reaction zone.

7. The process of claim 5 wherein recovered $BF_3$ is sent to a reaction zone.

8. The process of claim 1 wherein a $BF_3$-promoter complex is present in catalytic amount in the reaction zone, and the $BF_3$-promoter complex is the reaction product of $BF_3$ and a composition selected from straight and branched alkanols of 1 through 20 carbon atoms, water, hydrocarbyl acids containing from 1 to 20 carbon atoms, organic esters, and ketones, ethers, and alkoxylated alkanols, polyhydric alcohols, and inorganic acids, and silica, and zeolites.

9. The process of claim 1 wherein the inert volatile material comprises nitrogen.

10. The process of claim 5 wherein the inert volatile material comprises nitrogen.

* * * * *

UNITED STATES PATENT AND TRADEMARK OFFICE
CERTIFICATE OF CORRECTION

PATENT NO.: 5,811,616

DATED: September 22, 1998

INVENTOR(S): Richard A. Holub, Scott D. Soltis

It is certified that error appears in the above-identified patent and that said Letters Patent is hereby corrected as shown below:

| Col. | Line | |
|---|---|---|
| 6 | 35 | reads "700°C.," should read --70°C.,-- |
| 8 | 29-30 | reads "and ketones," "and alkoxylated alkanols," "and inorganic acids," "and silica," delete each instance of "and" |

Signed and Sealed this

Twenty-sixth Day of January, 1999

Attest:

Attesting Officer

Acting Commissioner of Patents and Trademarks